United States Patent [19]
Jaker et al.

[11] Patent Number: 5,676,688
[45] Date of Patent: *Oct. 14, 1997

[54] VARIABLY INFLATABLE MEDICAL DEVICE

[75] Inventors: Marc L. Jaker; Anna Maria Bigonzi-Jaker, both of New Brighton, Minn.

[73] Assignee: RTC, Inc., St. Paul, Minn.

[*] Notice: The term of this patent shall not extend beyond the expiration date of Pat. No. 5,531,717.

[21] Appl. No.: 676,581

[22] Filed: Jul. 1, 1996

Related U.S. Application Data

[63] Continuation-in-part of Ser. No. 384,571, Feb. 6, 1995, Pat. No. 5,531,717.

[51] Int. Cl.⁶ ................................................. A61M 29/00
[52] U.S. Cl. ........................ 606/195; 604/104; 606/198
[58] Field of Search ............................. 604/271, 171, 604/264, 349, 96, 104, 105, 106; 128/DIG. 25; 600/29–31; 606/195, 192, 198, 191, 196, 193, 194, 197

[56] References Cited

U.S. PATENT DOCUMENTS

| | | |
|---|---|---|
| 3,084,693 | 4/1963 | Cathcart . |
| 3,332,424 | 7/1967 | Minteer . |
| 3,421,509 | 1/1969 | Fiore . |
| 3,583,391 | 6/1971 | Cox et al. . |
| 3,850,720 | 11/1974 | Collins . |
| 3,866,601 | 2/1975 | Russell . |
| 4,085,757 | 4/1978 | Pevsner .......................... 606/195 |
| 4,251,305 | 2/1981 | Becker et al. . |
| 4,327,735 | 5/1982 | Hampson . |
| 4,364,392 | 12/1982 | Strother et al. .................... 606/195 |
| 4,652,259 | 3/1987 | O'Neil . |
| 4,743,258 | 5/1988 | Ikada et al. . |
| 4,946,440 | 8/1990 | Hall . |
| 5,181,921 | 1/1993 | Makita et al. ..................... 606/195 |
| 5,376,085 | 12/1994 | Conway et al. . |
| 5,531,717 | 7/1996 | Roberto et al. . |

FOREIGN PATENT DOCUMENTS

| | | |
|---|---|---|
| 0 247 559 A1 | 12/1987 | European Pat. Off. . |
| 1958561 | 6/1970 | Germany . |

*Primary Examiner*—Mark Bockelman
*Assistant Examiner*—Ronald K. Stright, Jr.
*Attorney, Agent, or Firm*—Snell & Wilmer L.L.P.

[57] ABSTRACT

A non-contaminating surgical introducer/dilator includes a variably inflatable tubular balloon membrane. The leading section of the membrane is circumferentially folded back over, forming a double walled tubular membrane. The open end of the tubular membrane is fixed to the stem of the guide. The stem of the guide is placed over the body cavity while the guide is slid over the introducer tube, thereby forcing the membrane through the guide and into the body cavity while simultaneously inverting the membrane over itself. Contact between the introducer tube and the abdominal/body cavity is inhibited and the passive transportation of pathogens into the cavity concomitantly prevented. The inflator tube is used to variably inflate the tubular balloon with sterile water or gas via a syringe/pump device to the desired pressure. Various methods of making and using the introducer/dilator of the present invention are also disclosed.

1 Claim, 3 Drawing Sheets

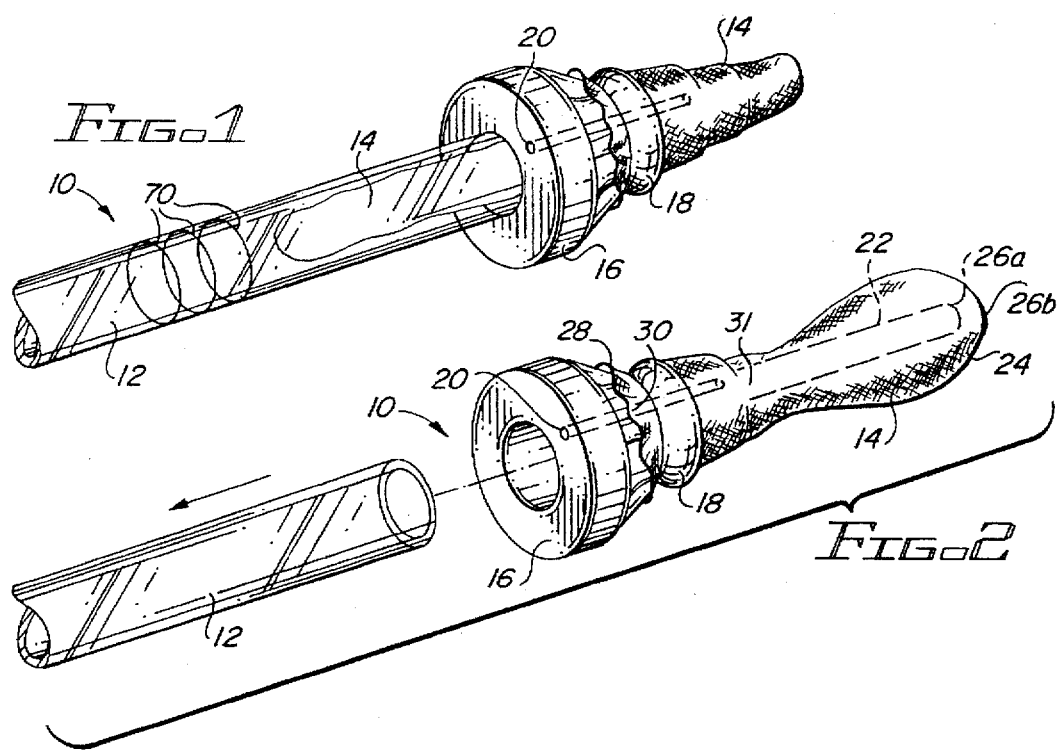
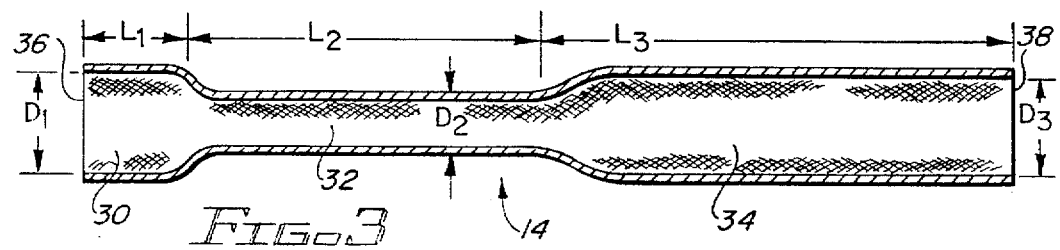
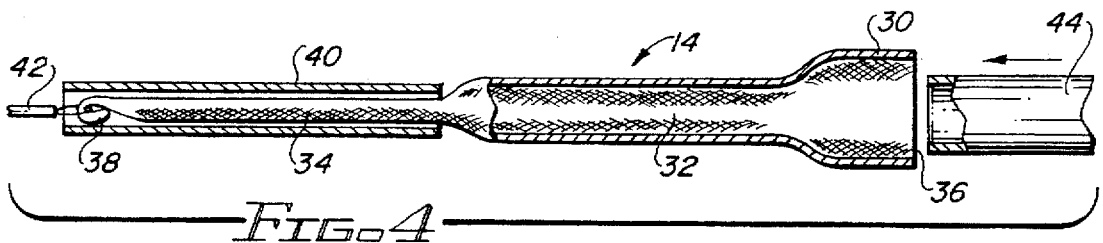
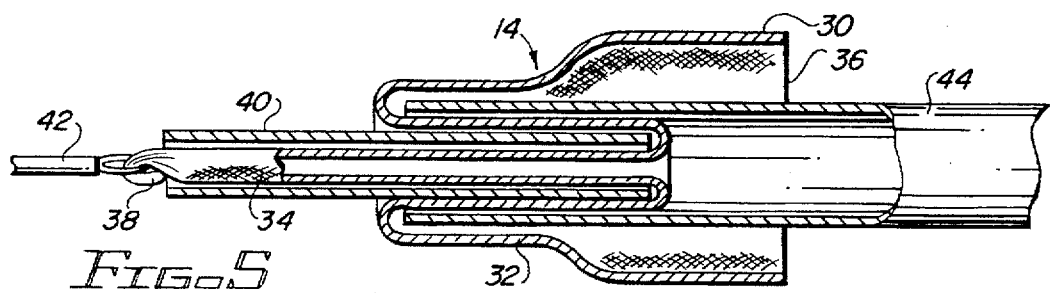

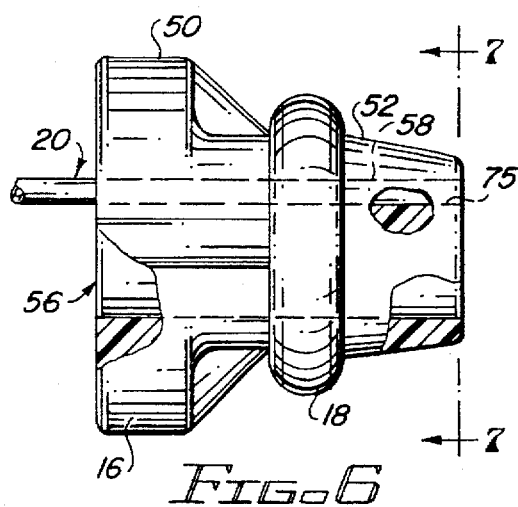
FIG. 6
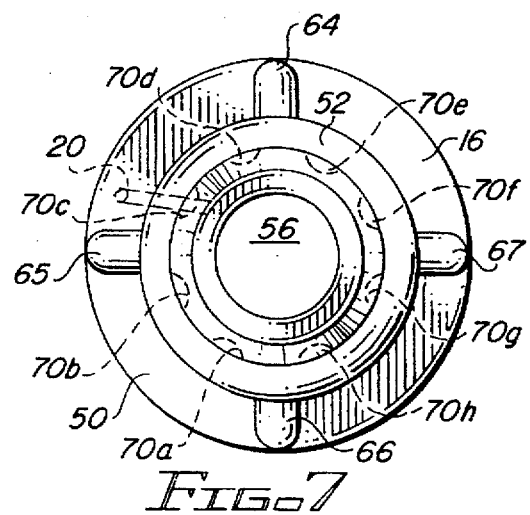
FIG. 7
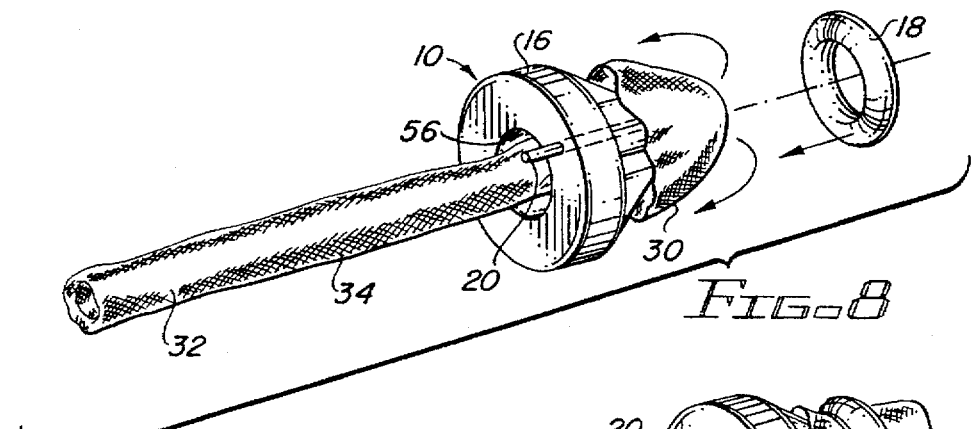
FIG. 8
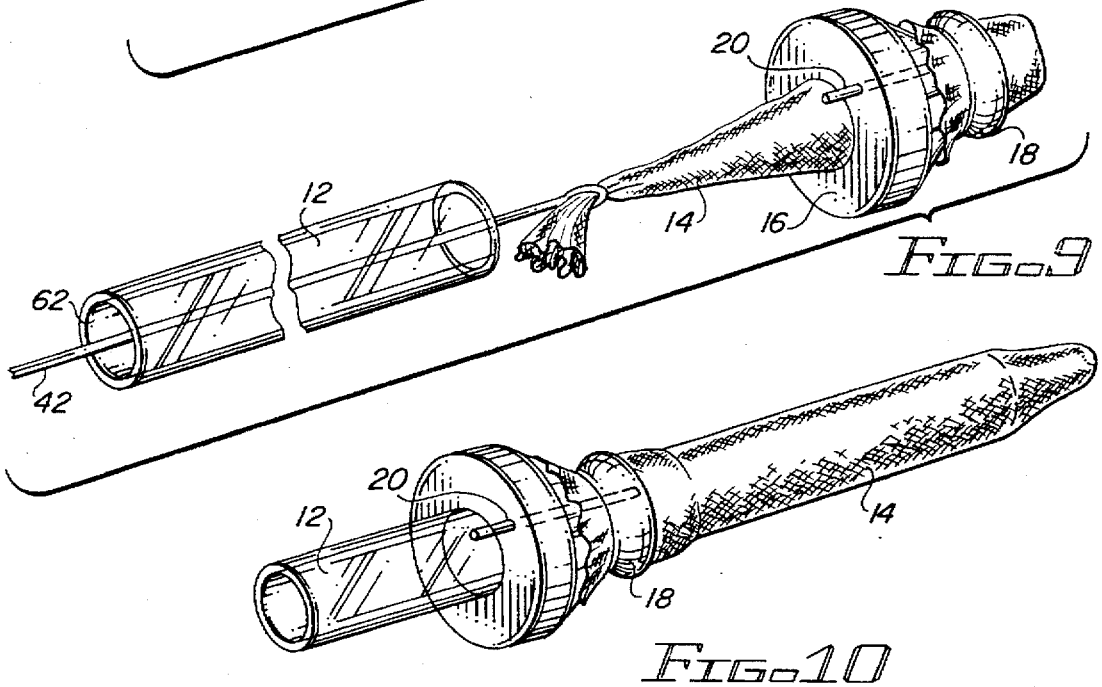
FIG. 9
FIG. 10 ns
VARIABLY INFLATABLE MEDICAL DEVICE

CROSS-REFERENCE TO RELATED APPLICATIONS

This application is a continuation-in-part of U.S. Ser. No. 08/384,571 filed Feb. 6, 1995, issued Jul. 2, 1996, as U.S. Pat. No. 5,531,717 entitled NON-CONTAMINATING PROBE AND METHODS OF MAKING AND USING SAME.

FIELD OF THE INVENTION

The present invention relates, generally, to sterilized medical probes and, more particularly, to a substantially anti-infectious variably inflatable device useful as an introducer, dilator, drainage stent, diffuser and/or the like.

BACKGROUND OF THE INVENTION

Introducers, dilators and drainage stents are used in a number of medical and related applications. It has been found that typical introducers-dilators, even if sterile when inserted into a patient, may contribute to infections by passing infectious material contained in the anatomical canal or other orifice when inserted in the patient. Treatment of such infections often involves the use of heavy medication (antibiotics) and may lengthen the patent's hospital stay, cause discomfort or lead to death.

As briefly noted above, it is believed that the insertion of the device, e.g. introducer/dilator, into a cavity may dislodge or otherwise attract infectious material (i.e., pathogens, virus, and bacteria which populate the initial points of entry) due to the frictional contact forces the introducer-dilator exerts on the body cavity walls as it is advanced. These pathogens are typically present on or in cavity walls or tissue. Once dislodged, the infectious material is carried, typically by the leading edge of the introducer-dilator, to internal organs or tissue, causing infection of the internal organ(s) or tissue. Even if no infectious or pathogenous material is dislodged, the frictional forces exerted on the cavity walls and surrounding tissue by conventional introducer-dilators tend to irritate or even possibly tear the cavity mucosa or tissue. While the irritation caused by this mechanical trauma exerted during penetration by the dilator is generally temporary, the fissures and thus blood contact experienced by the patient can be nonetheless significant.

Dilators are also used for a variety of other medical applications (i.e., urinary drainage, angioplasty arterial dilator, neurologic drainage stent, surgical drainage, wound drainage, Foley catheter alternative, female/male incontinence device, feeding tube/sheath, tracheal tubes, access tubes or plugs, etc.). The use of these devices in these applications also tends to be accompanied by an increase in the risk of infection, again typically as a result of the device pushing bacteria and other unwanted infectious material into the body cavity into which it is inserted.

In microvasive abdominal surgery, the objective is to make the incision as small as possible, but a small incision can limit the use and type of surgical devices. Certain body tissues (i.e., the first epidermal layer) have some elasticity and can be slowly stretched to larger diameters without traumatizing the tissue. The stretching (dilation) of the epidermal layers allow larger surgical tools and fiber optic viewing devices to be inserted into the body cavity. The use of larger surgical tools can be much more functional and effective than smaller devices, thus allowing more efficient and more successful surgeries. Successful surgery reduces trauma to the patient, shortens the recovery/healing time, and consequently, the quicker recovery would, in turn, lower health care costs. To stretch the epidermal layer, an effective space-saving dilator is needed to avoid the second introduction into the body cavity of the introducer.

These disadvantages are also encountered in other applications in which a device is used as a drainage stent and is inserted into a body cavity to either drain or inject internal fluids, or for other diagnostic procedures. For example, a drainage stent may also cause movement of infectious material or irritation to the canal or orifice into which the drainage stent is inserted.

When draining fluids from a body cavity or when injecting fluids into a body cavity, certain particulates may need to be separated or dispersed from the fluid. Existing filtration dispersion devices are composed of woven or layered "grid"-type patterns having greater than 0.010 wall section thickness and are principally used for the filtration/separation of small to large size particles within a fluid medium. The filtration or separation of particulate substances is currently accomplished before the insertion of the fluids into the body cavity (outside). Only after the fluid is filtered can the fluid be injected into the non-occluding diffuser. A biocompatible material with hole sizes under 0.010, and less than 0.010 thickness is needed, that can simultaneously provide bio-barrier and diffusion or filtration at a precise location with precise hole/filtration diameter of particulate while the fluid is injected or pressured through the introducer-dilator/diffuser membrane.

There thus exists a long-felt need to ameliorate the disadvantages occasioned by use of known medical introducer/dilators. There is a particular need for an introducer/dilator that does not cause infectious material to be carried or otherwise passed to the surgical cavity, which occupies less space for itself and provides greater slip (less friction), better access for the surgical instrument in one step.

Other catheters/dilators are known which purport to address these dilator problems; for example, the catheters/dilators shown in U.S. Pat. No. 3,421,509 issued to Fiore on Dec. 17, 1965; U.S. Pat. No. 3,084,693 issued to Cathcart on Apr. 9, 1963; DE 1958561 issued to American Hospital and published on Jun. 11, 1970; and IOP-A-247 559 issued to Sterimed and published on Dec. 2, 1987. While the catheters/dilators described in these references purport to address these problems, the catheter/dilator constructions of these references are medically unacceptable and, in practice, are inferior in performance to or considerably more complex than the dilator of the present invention. Moreover, some of the known catheter/dilator constructions simply do not work at all.

SUMMARY OF THE INVENTION

The present invention provides a non-contaminating introducer/dilator which addresses the aforementioned drawbacks of presently known introducer/dilators.

A preferred exemplary embodiment of the present invention provides, inter alia, a guide ring, a snap retention ring, an inflator tube, an introducer tube and an elongated, flexible tubular balloon membrane preferably comprising a polytetrafluoroethylene (PTFE) resin disposed within the guide ring assembly. The membrane is lubrous, thin (generally on the order of less than the thickness of a human hair), strong and very pliable.

The non-contaminating device of the present invention preferably includes a protective membrane (sheath) comprising modified polytetrafluoroethylene resin or a derivative thereof. In accordance with one aspect of the invention, a polyvinyl chloride (PVC) introducer tube suitably cooperates with the PTFE membrane such that upon insertion of the introducer/dilator into a cavity, sliding frictional contact between the introducer tube and the body cavity is inhibited and the passive transportation of pathogens in the cavity concomitantly prevented. An inflator tube, inserted into the guide ring assembly between the membrane walls, is used to variably inflate the balloon with e.g. sterile water, via a syringe device to the desired volume or pressure.

An alternative embodiment of the present invention includes a PTFE membrane with laser burned, sealed edge microscopic holes (with specific diameter and locations thus created) for the filtration-separation of particulates or introduction of drugs such as antibiotics while simultaneously sealing the body cavity and allowing a medical instrument to pass through it's center lumen, beyond the balloon's length.

The apparatus of the present invention, as will be described in greater detail herein, facilitates insertion of an introducer/dilator into a body cavity in a manner which effectively lessens the tissue damage caused by the frictional forces exerted by typical introducers/dilators and substantially inhibits the dragging of certain pathogens to internal tissue or organs during the introducer/dilation surgical procedure. Methods of making and using the dilator of the present invention are also disclosed.

BRIEF DESCRIPTION OF THE DRAWINGS

Preferred exemplary embodiments of the present invention will hereinafter be described in conjunction with the appended drawing figures, wherein like numerals denote like elements and:

FIG. 1 is a perspective view of a device in accordance with one embodiment of the present invention;

FIG. 2 is a perspective view of the device of FIG. 1 illustrating the inverted inflated tubular balloon assembly and with the introducer removed;

FIG. 3 is a cross sectional view of a preferred embodiment of a membrane useful in a device in accordance with the present invention prior to folding and assembly into the device of FIGS. 1 and 2;

FIG. 4 is a side elevational view of the membrane of FIG. 3 during a first part of a preferred folding operation;

FIG. 5 is a side elevational view of the membrane of FIG. 3 during a further aspect of a preferred folding operation;

FIG. 6 is an enlarged side elevational view of a guide assembly, including a snap ring which is useful in connection with a device in accordance with the present invention;

FIG. 7 is an end view of the guide assembly of FIG. 6 taken along the line 7—7 of FIG. 6; and FIG. 8 is a side elevational view showing the attachment of a membrane to the guide assembly in accordance with a preferred aspect of the present invention;

FIG. 9 is a side elevational view showing the loading of the membrane into an introducer tube and insertion of the introducer tube through the guide assembly;

FIG. 10 is a perspective view showing use of a device in accordance with the present invention and movement of an introducer tube through the guide assembly to unfold the membrane;

DETAILED DESCRIPTION OF PREFERRED EXEMPLARY EMBODIMENTS

Figure 11:
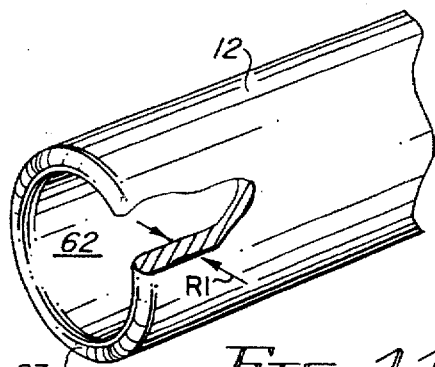
FIG. 11 is a sectioned perspective view showing one type of introduction tubing useful in accordance with the present invention.

While the way in which the present invention addresses the aforementioned disadvantages of the prior art is described in greater detail below, in general, a device 10 in accordance with the present invention includes a variably inflatable tubular balloon-like sheath (membrane) that inverts upon insertion of introducer/dilator 10 into an anatomical orifice or cavity.

With reference to FIG. 1, in general, device 10 comprises an introducer tube 12, a membrane 14, a guide 16 and a retaining device 18. In accordance with a preferred aspect of the present invention, and with momentary reference to FIG. 2, in use, preferably, introducer tube 12 is removed from introducer/dilator 10 and an aspect of membrane 14 is inflated through the inflow of fluid through stem 20 such that a balloon-type introducer/dilator 10 is obtained.

While a preferred exemplary embodiment of the present invention will be described with reference to device 10 as a surgical introducer/dilator, it should be appreciated that this description is for purposes of illustration of the invention, and while it describes a preferred embodiment thereof, the invention is not so limited. Various other devices as are now known or hereafter devised by those skilled in the art in light of the subject disclosure are within the scope of the invention. For example, device 10 may be suitably configured as a urinary drainage device, an angioplasty arterial dilator, a neurologic drainage stent, a surgical drainage device or, wound drainage, a Foley catheter alternative, a female/male incontinence device, a feeding tube/sheath, a tracheal tube, an access plug, or filtration device and/or the like. Preferably, introducer/dilator 10 comprises an introducer, a dilator, a plug or a medication applicator as will be herein described.

While the specific arrangement of the elements may be varied, in accordance with a preferred aspect of the present invention, membrane 14 preferably comprises a double tube configuration comprising, as shown best in FIG. 2, which includes an inner tube 22 and an outer tube 24. Preferably, and with continued reference to FIG. 2, inlet (stem) 20 extends from guide 16 into a space between tubes 22 and 24 such that as fluid (e.g. air or water) is passed into and through stem 20, outer tube 24 is caused to inflate and inner tube 22 remains uninflated. With continued reference to FIG. 2, tubes 22 and 24 of membrane 14 preferably have a common leading edge denoted at 26a and 26b respectively, and respective trailing edges 28 and 30. Membrane 14 is preferably suitably configured such that leading edge 26a forms an open end communicating with a lumen 31 which passes through tube 24. On the other hand, leading edge 26b forms a closed end such that tube 26 is substantially sealed at the leading edge. Preferably, trailing edges 28 and 30 are each suitably sealed to guide 16, such as, for example, through use of retainer 18.

The way in which introducer/dilator 10 can be fabricated and inserted for use may also vary based upon the application. From the general description contained herein various methods of manufacture and use will be readily appreciated by those skilled in the art. Accordingly, the following description of preferred ways should be viewed as illustrative only.

In accordance with one aspect of the present invention, and as previously briefly mentioned, preferably membrane 14 is of unitary construction and is suitably manipulated such that tubes 22 and 24 are evident. Of course, should it be desired, separate tubes joined at the leading edge (i.e. 26a, 26b) and open at the trailing edge (i.e. 28, 30) may be employed. Preferably, however, membrane 14 is configured as a unitary element such that it can be inverted prior to use to form tubes 22 and 24 when membrane 14 is, for example, withdrawn from introducer 12.

For example, and in accordance with a preferred aspect of the present invention, with reference to FIG. 3, membrane 14 preferably evidences three discrete sections 30, 32 and 34. Preferably, membrane 14 evidences a length L which equals the sum of the lengths $L_1$, $L_2$ and $L_3$ of sections 30, 32 and 34, respectively. While length L may vary as appropriate for particular applications, suitably length L varies from about 8 to about 40 cm, more preferably about 10 to about 25 cm and optimally about 10 to about 20 cm. Of this length, preferably lengths $L_1$ and $L_2$ of sections 30, 32 approximately equal the length of $L_3$ of section 34. As will be described in greater detail herein, in accordance with a preferred aspect of the present invention, preferably section 34 is folded over sections 30 and 32 such that the edge 36 and the edge 38 mate and can each be attached to guide 16.

With continued reference to FIG. 3, section 30 preferably evidences a diameter $D_1$, section 32 preferably evidences a diameter $D_2$, and section 34 preferably evidences a diameter $D_3$. Suitably, diameters $D_1$ and $D_3$ are similar, and preferably approximately equal. In accordance with a preferred aspect of the present invention, diameters $D_1$, $D_2$ and $D_3$ will vary depending upon the application and the size of tubing used for introducer 12. The sizing of membrane 14 also should take into consideration the tensilizing and stretching or other working of membrane prior to fabrication in device 10, as will be discussed in greater detail below.

Membrane 14 preferably comprises a thin, flexible polymeric material. Advantageously, membrane 14 has sufficient lubricity to smoothly slide out of and over the exterior of, for example, introducer tube 12. Thus, any suitable material having sufficient slip, strength, integrity, flexibility and lubricity may be utilized in accordance with the present invention to form membrane 14, provided the material has sufficient strength and flexibility to be medically acceptable when in use.

In accordance with a preferred aspect of the present invention, membrane 14 comprises a polytetrafluoroethylene resin, a modified PTFE resin, or combinations thereof. In accordance with a particularly preferred aspect of the present invention, membrane 14 is formed from a sintered PTFE film formed by skiving it off a billet to a thickness of less than 0.004 in., preferable on the order of about 0.001 in. The PTFE billet is preferably a modified PTFE, optimally either Hoechst TFM 1700 or TFM 1702 or other chemical compound available from DeWall Industries of Saunderstown, R.I. under the names DW/200, and DW/220 respectively or other processors. Such material comprises a modified PTFE polymer, modified by the addition of a small amount of perfluoro propyl vinyl ether (PPVE). It is believed that the addition of PPVE causes the PTFE to be more amorphous and more plasticized than pure crystalline PTFE.

Such modification also permits the film to be heat sealed upon itself (i.e., interfacial fusion), which is preferable in accordance with various aspects of the present invention.

In accordance with a further preferred aspect of the present invention, membrane 14 having multiple global sources may also comprise a modified PTFE resin available from DuPont under the name Mitsui-DuPont TG 70-J which has been sintered into billets, annealed, and skived to a thickness of on the order of 0.001 in. Additionally, it should be appreciated that other PTFE films may be suitably used as may be now known or hereafter devised by those skilled in the art. For example, PTFE homopolymers or copolymers with comonomers like PPVE, PFA and the like may be suitably used. It is important, however, that the film be usable to form membrane 14 which when used in connection with introducer tube 12 can be easily withdrawn, (i.e. does not "lock") when membrane 14 is (inverted) withdrawn in a "dry" state.

As previously noted membrane 14 preferably comprises a tube, the walls of which preferably have a thickness of less than about 0.004 in., more preferably less than about 0.0025 in., and optimally less than about 0.001 in. It has been found that one way of forming such a tube is by joining together two (2) film layers one on top of the other. Specifically, and in accordance with a preferred aspect of the present invention, once films having a thickness of less than 0.004 in. are obtained, they are suitably arranged to form a tube. Preferably, two layers of the film are placed one on top of the other and the longitudinal edges thereof heat sealed in a conventional manner, for example, through the use of heat sealing bars.

To improve the slip, strength and flexibility of membrane 14, it is preferable that membrane 14 be suitably tensilized or otherwise processed. As those skilled in the art will appreciate, tensilizing of polymeric films can be accomplished in a variety of ways. In accordance with one aspect of the present invention, tensilizing can be accomplished through any conventional or hereafter devised method. It has been found, for example, that simply working the membrane formed of a sintered PTFE film such as in one's fingers, provides a modicum of flexibility and improved strength, as may other tensilizing devices such as pin rollers, and the like. A tensilizing fixture such as that shown in U.S. Pat. No. 5,531,717 may also be employed. In accordance with this aspect of the present invention, film 14 may be elongated on the order of from about 25 to about 300 percent, more preferably from about 50 to about 200 percent, and optimally to about 125 to 150 percent.

Preferably, membrane 14 is incrementally stretched (enhanced) and shrinked about the mid-section length, e.g. section 32, and tensilized about the trailing section 34. The trailing section 34 of the membrane most efficiently slips if it is tensilized because the tensilizing tends to reduce the O.D., thereby tending in the practice of the invention to dictate and govern all other component dimension ratios.

With momentary reference to FIGS. 1 and 2, as shown, in use of device 10, membrane 14 is inverted (i.e. folded over) such that section 34 is inverted and placed inside sections 30 and 32 and such that the respective ends 36 and 38 of membrane 14 substantially mate. While the way in which membrane 14 can be inverted may vary, in accordance with one aspect of the present invention, membrane 14 is inverted through the use of inversion tubes. With reference to FIGS. 4 and 5, for example, an end 38 of trailing section 34 is preferably inserted into a first inversion tube 40, such as through use of any looped pulling device 42. Inversion tube 40 can be flexible or rigid but should enable easy insertion of membrane 14 therewithin and a sufficient durability to enable the folding operation now being described. As shown best in FIG. 4, preferably the diameter of tube 40 is selected such that it is smaller than $D_2$, i.e. the diameter of section 32, and as such, section 34 is preferably squeezed into tube 40.

With continued reference to FIGS. 4 and 5, once section 34 is within tube 40, a second inversion tube 44 preferably evidencing a larger outside diameter is inserted into section 30 of the membrane 14 past edge 36. The diameter of tube 44, while larger than the diameter of tube 40, is preferably smaller than $D_1$, i.e. the diameter of section 30, such that as tube 44 is inserted passed edge 36, tube 44 encounters the inner wall of membrane 14 which joins sections 30 and 32. With continued reference to FIG. 5, tube 44 is thereafter moved over the top of first inversion tube 40, thus inverting a portion of section 32 and section 30 of membrane 14 over first inversion tube 40 and section 34 contained therewithin. Once fully inverted, for example, by further movement of tube 44 relative to tube 40, sections 32 and 30 circumscribe inversion tube 40. Thereafter, inversion tubes 40 and 44 are carefully retracted. The folded (now double-walled) membrane 14 now evidences inner tube 22 which comprises section 34 of membrane 14 and outer tube 24 which comprises membrane sections 30 and 32.

Preferably, membrane 14 once inverted is attached to guide 16. With reference to FIG. 6, guide 16 preferably comprises any device capable of accommodating the sealing of the membrane 14 thereto, and as discussed in greater detail below permits fluid to be passed into stem inflator tube 20.

In general, guide 16 includes an enlarged grip portion 50 and membrane receiving portion 52; retainer 18 suitably cooperates with portion 52 to retain membrane 14, and in particular ends 36 and 38 thereof in contact therewith. In accordance with one aspect of the present invention, guide 16 evidences a nipple configuration, such as shown in FIG. 6. An axial passageway 56 extends through guide 16 to permit initial passage of membrane 14, and in use, passage of introducer 12.

Guide 16 may comprise any suitable material such as metal, plastic or the like. Guide 16 suitably comprises a material having a relatively low frictional coefficient such as, for example, polyethylene-based materials. Irrespective of the particular material used for guide 16, the inner bearing surface thereof optimally exhibits sufficient lubricity to permit easy passage along the outside of introducer tube 12 during use.

Guide 16 is suitably configured to permit a user to grasp guide 16 such as about enlarged or grip portion 58. Additionally, preferably guide 16 includes a ribbed body spanning between portions 50 and 52. For example, and with reference to FIG. 7, the body of guide 16 preferably includes a plurality of ribs 64, 65, 66, and 67, which are suitably equidistantly spaced about the circumference of guide 16. Suitably arranged between ribs 64–67 are a plurality of apertures 70a–70h. The outer diameter of portion 52 is preferably sufficiently sized relative to membrane 14 such that a "force-fit" engagement between membrane 14 and guide 16 is maintained.

With continued reference to FIG. 7 and additional reference to FIG. 6, guide 16 includes stem (fluid inlet) 20. In accordance with preferred aspects of the present invention, inlet 30 may comprise any device enabling the passage of fluid, and thus, inflation of outer tube 24. In accordance with one aspect of the present invention, inlet 20 comprises a straw-like device which is pushed forward and through a lumen 58 in the guide 16 and is positioned in a trough 75 located on guide 16 beneath lumen 58. Preferably, inlet 20 lies within trough 75 and is, thus, less susceptible to being crushed under the load force of retainer 18. By the incorporation of a trough 75 directly underneath the lumen 58 in the guide 16, guide 16 is designed to accommodate the sealing of membrane 14 at the diameter and allow for inlet 20 to be open, not pinched shut.

With reference now to FIG. 8, membrane 14 is preferably attached to guide 16 by passing a portion of membrane through lumen 56 and attaching another portion to guide 16. Preferably, membrane 14 is rolled tight at end 38 and inserted through passageway 56 of guide 16. A loope device 42 (not shown in FIG. 8) may be used. End 36 is then circumscribed around portion 52 of guide 16 in such a way that end 38 is passed through passage 56. Open end 28 is positioned under stem 20 and open end 30 is suitably positioned over stem 20.

Retainer 18 is then circumscribed over portion 52 of guide 16, thereby securely affixing membrane 14 to guide 16. Retainer 18 is suitably placed over and force fit to hold membrane 14 snugly in membrane-receiving area 52. Thus, the stem 20 lies between open end 30 and open end 28 of the membrane 14 and underneath the retainer 18. Therefore, membrane 14 has a center lumen for access to, or drainage from, for example, a body cavity. A surgical instrument can also be guided through the tubular balloon membrane.

Retainer 18 may be composed of any suitable material but preferably comprises a polymeric material having sufficient rigidity while at the same time sufficient flexibility to fit over and snap onto guide 16. Preferably, retainer 18 is formed from a polyurethane resin having a Shore A hardness in the range of about 90 durometer, or other suitable elastomeric thermoplastic or thermoset material.

With reference to FIG. 9, once membrane 14 is suitably attached to guide 16, introducer 12 is preferably inserted into passageway 56, with the portion of membrane 14 not attached to guide 16 passed into introducer 12. For example, a looped device, like device 42, may be used to grasp the available end of membrane 14 and pull that end through the lumen 62 of introducer 12. With continued reference to FIG. 9, using the looped pulling device 42, an end of the membrane 14 is inserted into loop of the device 42 and pulled inside tube 12. After tube 12 is positioned between the membrane 14 and lumen 362 of the guide 16, the pulling device 70 is disengaged and removed. However, membrane 14 can be loaded into tube 12 in any suitable manner.

Introducer tube 12 preferably comprises a flexible biocompatible polymeric material, for example an FDA approved material; but it could be rigid, even metal, like 420 stainless steel, depending on the application. In accordance with a preferred aspect of the invention, introducer tube 12 comprises a polymeric material having a Shore A hardness in the range of about 55 durometer to about 160 durometer, and preferably about 60 durometer to about 90 durometer, and more preferably in the range of about 65 durometer to about 75 durometer. Suitable polymeric materials preferably include thermoplastic polymers, for example polyurethanes, polyvinyl chlorides, or the like (e.g., medical grade polyvinyl chloride, PVC). Such thermoplastic polymers may be natural or synthetic, and may be modified or further enhanced by the addition of lubricants such as glycerin, glycol and possibly blended with antimicrobial agents or the like to treat pre-existing infection beyond the length of the membrane assembly. Other conventional addresses now known or hereafter devised by those skilled in the art also may be suitably included.

It should be understood that any material may be used to suitably form introducer tube 12, and that the above examples are provided for illustration purposes only. A particularly preferred material for introducer tube 12 is polyvinyl chloride (PVC) tubing having a Shore A hardness in the range of about 75+/−5 durometer. The preferable PVC introducer tube 12 can be provided in various diameters, primarily depending upon its use. As will be appreciated by those skilled in the art, introducer tube 12 when used as a dilator has a circumference of about 8 to about 100 French (and thus a corresponding diameter of about 2.5 to about 30 mm).

Introducer tube 12 preferably has a length characteristic of conventional dilators, tubes or probes. For example, when introducer/dilator 10 is used as an incontinence device for males, it will generally have a length of from about 10 cm to about 20 cm, typically about 10 cm; when utilized as an incontinence device for females, introducer tube 12 generally will have a length of from about 5 cm to about 15 cm, typically about 7 cm. With reference to FIG. 11, tube 12 preferably has a leading edge 63 at which lumen 62 terminates. In accordance with a preferred aspect of the present invention, edge 63 is suitably rounded to evidence a radius R1, which configuration aids in the unfolding of membrane 14 from lumen 62 as will be described in greater detail below.

While various combinations of materials for membrane 14 and introducer tube 12 may be used in the context of the invention, it is important that the material and/or materials selected exhibit sufficient non-adhesiveness and/or anti-frictional characteristics such that the frictional force exerted by membrane 14 on the introducer tube 12 as membrane 14 is withdrawn therefrom is less than the frictional force exerted by introducer tube 12 on membrane 14. Preferably, the materials are selected such that membrane 14 can be withdrawn from introducer tube 12 easily, without the use of lubricants, hydraulics, pneumatic or mechanical assists. Stated another way, introducer tube 12 and membrane 14 suitably are formed of materials which enable membrane 14 to be easily withdrawn from introducer tube 12 in a "dry" state without the need for lubricants applied to either membrane 14 and/or introducer tube 12.

It has been found that introducer tube 12, comprising PVC, works particularly well with the preferred PTFE membrane 14. A particularly preferred device 10 in accordance with the present invention, preferably comprises an introducer tube 12 formed of PVC having a circumference in the range of 8 to 100 French and a polytetrafluoroethylene membrane 14 having a thickness in the range of less than about 0.004 in., preferably 0.0005 to about 0.0025 in. provided a medically acceptable introducer/dilator which is convenient to use.

As will be appreciated, the respective sizes of guide 16 and membrane 14 may be chosen to facilitate their convenient movement over the exterior surface of introducer tube 12. For example, if the diameter of introducer tube 12 at leading edge 122 is in the range of about 5 mm, then the diameter of membrane 14 and the inner diameter of guide 16 in accordance with one aspect of the invention should be at least about 6 mm.

Once membrane 14 is suitably attached to guide 16, membrane 14 is preferably trimmed to an appropriate length and shape, for example, angling the trailing edge to permit enhanced release from introducer 12. Preferably, membrane 14 is trimmed to an operational length of between about 8 and about 40 cm, more preferably between about 16 and about 20 cm. Membrane 14 typically exhibits a length less than that of introducer tube 12. For example, membrane 14 is desirably in the range of about 10 to about 40 cm, and preferably about 16 and about 20 cm, while the length of introducer is considerably longer. With reference to FIG. 1, a plurality of calibrations 70, (e.g. one or more lines or other visual or other detectable markings), may be optionally imprinted on the exterior surface of introducer tube 12. Calibrations 70 are preferably oriented to enable the user to determine the position of membrane 14 as introducer/dilator 10 is inserted into a body cavity, a preferred process by which that is accomplished which will now be described.

In accordance with a preferred aspect of the present invention, device 10 is preferably inserted into a body cavity or orifice through use of introducer 12. It should be appreciated, however, that this is but one manner of use, and although preferred, is provided herein for purposes of illustration.

Figure 12:
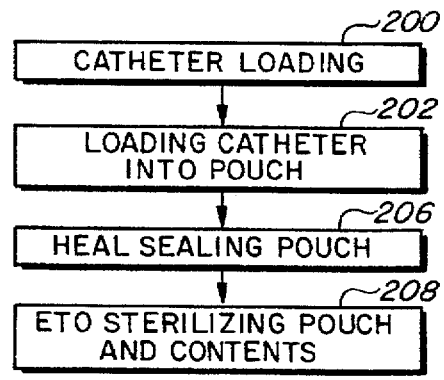
FIG. 12 is a flow chart illustrating the steps of a sterilization method useful in sterilizing a device in accordance with the present invention.

With reference again to FIG. 1, once membrane 14 is suitably loaded (snug) within introducer tube 12, guide 16 is located near the leading edge of introducer 12, with the majority of membrane 14 contained within lumen 62 of introducer tube 12. Device 10 is then ready for introduction into a body cavity or orifice. With reference to FIGS. 1, 10 and 12, preferably introducer 12 is urged into the cavity, and as this is accomplished, membrane 14 is unfolded.

Guide 16 is preferably placed over the surgical cavity (not shown) and introducer tube 12 is urged into the cavity, thereby forcing the membrane 14 through lumen 56 of the guide 16 and into the surgical cavity. Simultaneously, membrane 14 is inverted over itself. (See FIGS. 1 and 10). Once the membrane 14 is fully inserted into the surgical cavity, the membrane 14 circumscribes the introducer tube 12; thus, contact between the introducer tube 12 and the patient's body cavity (not shown) is substantially, if not entirely, prevented during insertion for the length of the membrane 14. More particularly, the membrane is laid out as the guide 16 is slid along the introducer tube 12 and thus remains interposed between the exterior wall of the introducer tube 12 and the patients' body cavity (e.g., abdominal cavity). Sliding frictional force is inhibited and the passive transportation of pathogens into the cavity concomitantly prevented.

Once the membrane 14 is totally unfolded and positioned inside the body cavity, see FIG. 12, introducer 12 can be withdrawn and tube 24 of membrane 14 can be suitably inflated. Alternatively, in those applications where it is desirable to leave tube 20 in place, membrane 14 attached to guide 16 can be removed. Such removal can be preceded by inflation of tube 24 of membrane 14, if desired.

In either case, tube 24 is preferably inflated by the passage of fluid into inlet 20 to suitably variably inflate the tubular balloon aspect of membrane 14. Such a fluid may be introduced via a syringe or pump device to a desired pressure. In accordance with various aspects of the present invention, the fluid may comprise gas, gels, jellies, lubricants or other fluids of various viscosity. Sterile water is preferably, and probably the most practical and efficient fluid for most procedures because it effectively adjusts to pressure and is biocompatible. The desired pressure is dependent on the medical procedure and the comfort of the patient or requirement of the attending physician. A valve (e.g. a pinch-off valve) (not shown) may be applied to inlet 20 to stabilize the balloon pressure before the syringe or pump 15 removed. Deflation of the balloon can be accomplished, for example, by extracting water via a syringe, pump, or by opening the valve.

If the tubular balloon membrane 14 is fully inflated and the PVC introducer tube is removed, membrane 14 can serve as an introducer/dilator or a surgical plug to stop or limit the loss of body fluids or surgical gases. The tubular balloon membrane 14 can create simultaneous pressure (when inflated) on both the surrounding tissue to the outside and on the internal tube to hydraulically restrict the flow in or out. Partially inflated, the tubular balloon is still retained in the body cavity, but acts as a retention or drainage device by allowing body fluids to drain out through the center lumen of the tubular balloon. The pressure in the tubular balloon membrane 14 determines the retention and out flow balance.

In certain applications, the removal of membrane 14 may be beneficial; as membrane 14 is removed, it may act as a unidirectional brush which aids in the cleansing of pathogens contained within the (e.g. urethral canal). That is, as membrane 14 is pulled back and removed from the body/surgical cavity, a wiping action occurs such that pathogens contained within the canal may be attracted to and moved outwardly from the body canal.

As will be appreciated, in use membrane 14 initially acts as a sheath, but it also displaces surrounding tissues and organs, while simultaneously allowing fluid access down through its center via the central lumen. The mechanical characteristics of the present invention, including its extremely high, dry slip which allow smoother, more efficient access of microvasive surgery instruments, therein reduces or eliminates the need for surgical lubricants, making procedures cleaner, quicker and less traumatic, thereby improving overall microvasive surgical techniques.

In accordance with one application of the present invention, for example, as a female incontinence device (and for some males), the mechanical characteristics of device 10 may serve to assist or retrain weak muscles, while allowing some flow when the bladder fills and pressure is elevated. As the pressure in the balloon is determined by its volume, as tube 24 of device 10 is brought towards the maximum O.D. volume of the balloon configuration tends to simulate the natural form of a body cavity (i.e., urethra) and flexes with the body. The same result occurs if the balloon aspect of membrane 14 is used as an indwelling access drainage dilator filled to 30–60% of the outer balloon wall volume. By anatomically conforming, the device provides sterile, comfortable social mobility for the patient.

The assembly comprising membrane 14, guide 16 and introducer tube 12 is preferably sterilized prior to use, such as prior to use as a surgical introducer/dilator. To that end, and with reference to FIG. 12, introducer/dilator assembly 10 is loaded into a conventional Chevron pouch having a dimension of about 20×3 in. with the leading edge first, and the pouch is sealed. With specific reference to FIG. 12, step 200 relates to assembly of the introducer/dilator in the manner described herein. Step 202 involves the loading of introducer/dilator assembly 10 into a pouch. Step 206 involves heat sealing of the pouch with introducer/dilator assembly 10 suitably contained therein. In accordance with step 206, conventional indicated at step 208, suitably sterilized such as through the use of ethylene oxide (ETO). In accordance with conventional sterilization procedures, the pouch is first exposed to ethylene oxide and then oxygen, and multiple exposures are cycled over predetermined periods of time.

Figure 13:
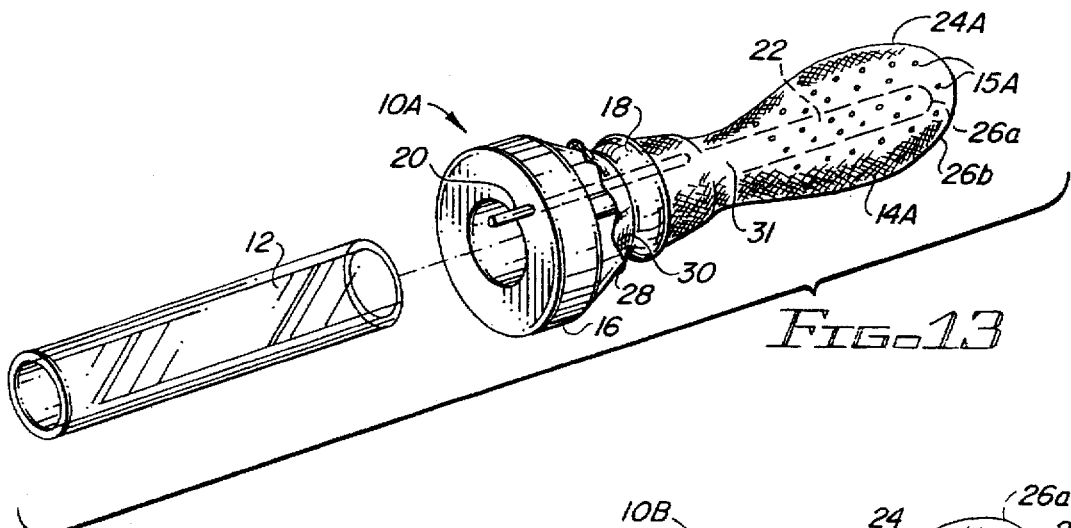
FIG. 13 is a perspective view of an alternative embodiment of a device in accordance with the present invention.

With reference to FIG. 13, an alternative embodiment of the present invention is shown wherein a device 10A includes a membrane 14A which contains at least one, but preferably a plurality of microscopic openings 15A through the surface of the membrane 14A which defines tube 24A. When membrane 14A is incorporated into device 10A, or any other probe, device 10A can be used as a filtration device. The filtration membrane 14A will optimally filter or disperse particulates (i.e., antibiotics, drugs, and the like) from the insertion fluid.

While openings 15A can be formed in any convenient manner, preferably openings 15A are 0.0001" (0.25 microns) or greater in diameter. A nominal size is 0.001"–0.002" in diameter (4–8 microns). The openings are optionally customized to any desired diameter, quantity and spacing across the membrane 14A surface. The openings are preferably fabricated by passing a laser source through the surface of membrane 14A. A laser source, preferably a YAG laser, is set at a frequency to impact the surface of membrane 14A at less than 1 second. To form the desired openings, the laser will melt/burn a microscopic area of the membrane 14A surface, while simultaneously sealing the edges of the opening. The sealing of the edges prevents the opening from further expansion or cracking under inflation pressures. Membrane 14A may then be subsequently annealed at 250–600 degrees (optimal annealing at 350–400 degrees). The annealing relieves the stress in the tensilized PTFE to allow the PTFE to withstand greater axial inflation pressures, as may exist upon expansion of the balloon.

Figure 14:
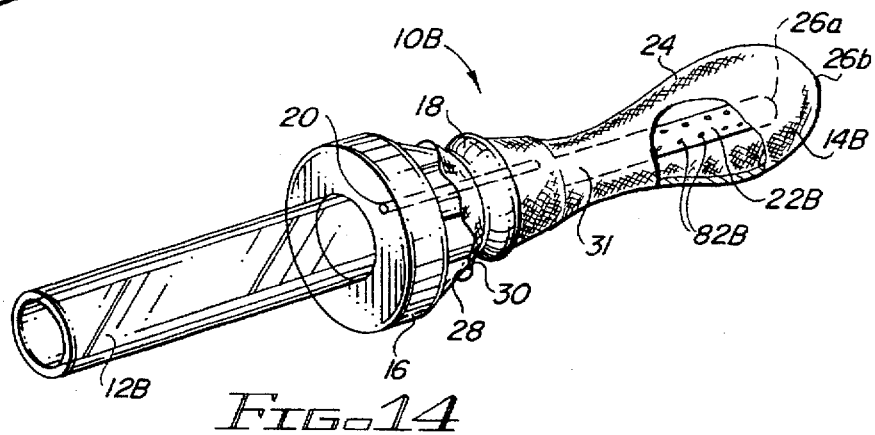
FIG. 14 is a perspective view of a further alternative embodiment of a device in accordance with the present invention.

With reference to FIG. 14, a further alternative embodiment of the present invention is illustrated with reference to the device 10B. In the context of this embodiment, at least one, but preferably a plurality of microscopic apertures 82B are provided in a tube 22B of the membrane 14B thereby providing for fluid communication between tube 22B and tube 24 of membrane 14B. In accordance with this aspect of the present, fluid may be passed into tube 12B then through tube 22B and into balloon tube 24, thereby avoiding the necessity of inlet stem 20 as used in connection with device 10. As will be appreciated, such fluid may be so communicated, for example, during insertion of membrane 14B into a cavity. Alternatively, after full insertion of membrane 14B into a cavity through use of an introducer tube 12, (not shown in FIG. 14) introducer 12 may be removed and a closed end introducer tube 12B inserted into device 10B, as shown, for the purpose of providing for the passage of fluid into tube 24.

It will be understood that the above description is of preferred exemplary embodiments of the present invention, and that the invention is not limited to the specific forms shown and described herein. For example, some or all of the components may be plasma surface-treated to enhance hydraelasticity. Further, various alternative configurations of device 10, particularly introducer tube 12, may be readily incorporated by those skilled in the art. These and other modifications may be made in the design and arrangement of the elements within the scope of the invention, as expressed in the appended claims.

We claim:

1. A variably inflatable device for insertion into a cavity, the device comprising:

a guide having a central lumen, and an air inlet;

a membrane attached to said guide defining a closed tube, an open tube and a double walled mid section spanning therebetween, said open tube in fluid communication with the cavity, said closed tube communicating with said air inlet and configured to be variably inflated;

an introducer disposed within said lumen of said guide to communicate with said membrane and urge said membrane into the cavity in use;

a retaining device frictionally received over a portion of said guide to secure said membrane to said guide.

* * * * *

UNITED STATES PATENT AND TRADEMARK OFFICE
CERTIFICATE OF CORRECTION

PATENT NO. : 5,676,688

DATED : October 14, 1997

INVENTOR(S) : Marc L. Jaker

Anna B. Bigonzi-Jaker

It is certified that error appears in the above-identified patent and that said Letters Patent is hereby corrected as shown below:

On Fig. 12, "Heal" is replaced by "Heat"

Signed and Sealed this

Seventeenth Day of March, 1998

Attest:

BRUCE LEHMAN

Attesting Officer

Commissioner of Patents and Trademarks